(12) United States Patent
Ji

(10) Patent No.: US 8,993,644 B2
(45) Date of Patent: *Mar. 31, 2015

(54) MEDICAL DEVICES FORMED FROM RECYCLED MEDICAL WASTE AND METHODS OF MANUFACTURE

(75) Inventor: Richard Ji, Temecula, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 507 days.

This patent is subject to a terminal disclaimer.

(21) Appl. No.: 12/562,355

(22) Filed: Sep. 18, 2009

(65) Prior Publication Data

US 2011/0071230 A1 Mar. 24, 2011

(51) Int. Cl.
| C08J 11/04 | (2006.01) |
| A61L 11/00 | (2006.01) |
| A61L 2/04 | (2006.01) |
| A61L 2/07 | (2006.01) |
| A61L 2/18 | (2006.01) |
| C08J 11/06 | (2006.01) |
| G06Q 10/00 | (2012.01) |

(52) U.S. Cl.
CPC . *A61L 11/00* (2013.01); *A61L 2/04* (2013.01); *A61L 2/07* (2013.01); *A61L 2/18* (2013.01); *C08J 11/06* (2013.01); *G06Q 10/30* (2013.01); *Y10S 241/602* (2013.01)
USPC .......... 521/40; 521/41; 521/46; 521/47; 521/48; 422/26; 422/292; 422/295; 422/298; 422/307; 422/309; 241/15; 241/24.18; 241/24.28; 241/602

(58) Field of Classification Search
USPC ........ 521/40, 40.5, 41, 45, 45.5, 46, 46.5, 47, 521/48, 49, 49.8; 528/480, 481, 499, 500, 528/502 R, 502 A, 502 C, 502 F, 503; 241/14, 241/15, 18, 24.1, 24.18, 24.22, 24.25, 241/24.28, 606, DIG. 38; 422/26, 27, 28, 422/31, 292, 295, 298, 299, 305, 307, 309
See application file for complete search history.

(56) References Cited

U.S. PATENT DOCUMENTS

| 5,075,057 A | 12/1991 | Hoedl |
| 5,271,500 A | 12/1993 | Szacon |
| 5,277,869 A | 1/1994 | Glazer et al. |
| 5,350,562 A | 9/1994 | Anthony |
| 5,395,681 A | 3/1995 | Hargarter et al. |
| 5,427,737 A | 6/1995 | Glazer et al. |
| 5,462,794 A | 10/1995 | Lindemann et al. |
| 5,508,004 A | 4/1996 | Held et al. |
| 5,557,905 A | 9/1996 | Harding |
| 5,558,280 A | 9/1996 | Morgan |
| 5,582,793 A | 12/1996 | Glazer et al. |
| 5,693,278 A | 12/1997 | Clements |
| 5,785,260 A | 7/1998 | Morgan |
| 5,824,745 A | 10/1998 | Brown |
| 5,830,396 A | 11/1998 | Higgins et al. |
| 5,830,419 A | 11/1998 | Held et al. |
| 5,833,922 A | 11/1998 | Held et al. |
| 5,876,544 A | 3/1999 | Yamamoto et al. |
| 6,053,314 A | 4/2000 | Pittman |
| 6,348,272 B1 | 2/2002 | Haveaux et al. |
| 6,509,537 B1 | 1/2003 | Krieg et al. |
| 6,712,207 B2 | 3/2004 | Panek, Jr. et al. |
| 6,792,662 B2 | 9/2004 | Samuel |
| 6,808,820 B2 | 10/2004 | Lee et al. |
| 6,881,493 B2 | 4/2005 | Haveaux et al. |
| 7,243,792 B2 | 7/2007 | Panek, Jr. et al. |
| 7,531,226 B2 | 5/2009 | Lee et al. |
| 7,596,844 B2 | 10/2009 | Japuntich et al. |
| 7,600,639 B2 | 10/2009 | Japuntich et al. |
| 7,877,849 B2 | 2/2011 | Panek, Jr. et al. |
| 2003/0038046 A1 | 2/2003 | Panek, Jr. et al. |
| 2003/0170157 A1* | 9/2003 | Aubert .................... 422/939 |
| 2003/0183705 A1 | 10/2003 | Christiani et al. |
| 2003/0213714 A1 | 11/2003 | Moats et al. |
| 2004/0099555 A1 | 5/2004 | Panek, Jr. et al. |
| 2005/0121343 A1 | 6/2005 | Miller et al. |
| 2005/0127579 A1 | 6/2005 | Suzuki |
| 2005/0218142 A1 | 10/2005 | Finnestad et al. |
| 2005/0228682 A1 | 10/2005 | Firestone, III |
| 2007/0068832 A1 | 3/2007 | Anderson et al. |
| 2007/0068834 A1 | 3/2007 | Smudde et al. |
| 2007/0069490 A1 | 3/2007 | Japuntich et al. |
| 2008/0058736 A1 | 3/2008 | Reshamwala |
| 2008/0067093 A1 | 3/2008 | Japuntich et al. |
| 2008/0067094 A1 | 3/2008 | Japuntich et al. |

(Continued)

FOREIGN PATENT DOCUMENTS

| DE | 271454 | 9/1989 |
| DE | 4319989 | 12/1994 |

(Continued)

OTHER PUBLICATIONS

"Red Bag Solutions: Providing the Best Solution for the Disposal of Infectious Red Bag Medical Waste", *Red Bag Solutions* @ redbag. com, (Feb. 24, 2010) 1 pg.

"Non-Final Office Action in U.S. Appl. No. 12/883,840", mailed Feb. 21, 2012, 17 pages.

"Machine Translation of DD 271454", 1 pgs.

"PCT IPRP & Written Opinion in PCT/US2010/049275, mailed Mar. 29, 2012", 7 pgs.

*Primary Examiner* — Francis Tischler
(74) *Attorney, Agent, or Firm* — Servilla Whitney LLC

(57) ABSTRACT

Methods of reclaiming plastic from plastic medical waste containers containing medical waste and manufacturing recycled medical devices are described. Recycled medical devices made from plastic medical waste containers containing medical waste are also described.

12 Claims, No Drawings

(56) References Cited

U.S. PATENT DOCUMENTS

| | | |
|---|---|---|
| 2008/0067100 A1 | 3/2008 | Japuntich et al. |
| 2008/0073231 A1 | 3/2008 | Clayton et al. |
| 2008/0073232 A1 | 3/2008 | Reshamwala et al. |
| 2008/0073251 A1 | 3/2008 | Reshamwala et al. |
| 2008/0140032 A1 | 6/2008 | O'Malley |
| 2009/0032423 A1 | 2/2009 | Japuntich |
| 2009/0068412 A1 | 3/2009 | Nahmias et al. |
| 2009/0110654 A1 | 4/2009 | Hagemann et al. |
| 2009/0120821 A1 | 5/2009 | Japuntich et al. |
| 2009/0145901 A1 | 6/2009 | Finnestad et al. |
| 2009/0230008 A1 | 9/2009 | Miller et al. |
| 2010/0041937 A1 | 2/2010 | Gonzalez |
| 2010/0062921 A1 | 3/2010 | Veiseh |
| 2010/0155400 A1 | 6/2010 | Finnestad et al. |
| 2010/0282623 A1 | 11/2010 | Reshamwala |
| 2011/0068036 A1 | 3/2011 | Ji et al. |
| 2011/0071230 A1 | 3/2011 | Ji |

FOREIGN PATENT DOCUMENTS

| | | |
|---|---|---|
| DE | 19726105 | 12/1998 |
| JP | H08-131531 | 5/1996 |
| JP | H08-182750 | 7/1996 |
| JP | 2002059082 | 2/2002 |
| JP | 2004-035164 | 2/2004 |
| JP | 2004-516163 | 6/2004 |
| WO | WO-91/01396 | 2/1991 |
| WO | WO-99/62566 | 12/1999 |
| WO | WO-00/54885 | 9/2000 |
| WO | WO-2008/039438 | 4/2008 |
| WO | WO-2008/106759 | 9/2008 |
| WO | WO-2011/035119 | 3/2011 |

* cited by examiner

MEDICAL DEVICES FORMED FROM RECYCLED MEDICAL WASTE AND METHODS OF MANUFACTURE

FIELD OF THE INVENTION

The present invention relates generally to methods of reclaiming and recycling plastics from comingled medical waste. More specifically, embodiments of the invention are directed to methods of reclaiming plastics from comingled infectious medical waste for use in making medical devices from reclaimed medical waste and to medical devices made from reclaimed comingled medical waste.

BACKGROUND

The disposal of medical waste is a significant concern from an environmental perspective. Medical waste, which is often infectious, is currently sterilized and relegated to a lifetime in a landfill. Even though many components of medical waste are considered recyclable, these components are not reused for fear of contamination from the infectious materials and the stigma associated with being medical waste and containing infectious matter. This results in the waste of a significant amount of otherwise recyclable materials and occupies valuable space in landfills.

Medical waste can include waste containers, plastics, sharps—both used and unused, broken glass, syringes, rubber components, blood, pathogens, fecal matter and other infectious agents. The medical waste components are usually comingled within a waste container. Sterilization can be carried out by a number of techniques including, but not limited to, autoclaving, gamma irradiating, exposure to ethylene oxide, exposure to microwaves, exposure to radio-frequency waves, and combinations of these techniques. Many of these techniques are not particularly desirable, as they can leave an unpleasant smell, traces of blood may still be seen, and the physical properties of the sterilized plastics can be altered. Therefore, the choice of sterilization technique can have an effect on the resulting sterilized material.

Recycling plastics is a fairly common practice where the plastics are from benign sources. However, plastic comingled with infectious waste typically is not recycled into useful products, especially not into medical devices. U.S. Pat. No. 5,833,922 describes a method for processing medical waste using radio-frequency electromagnetic radiation to obtain reclaimed plastic and refuse-derived fuel, however, there is no description of use of the reclaimed plastic in medical devices other than sharps disposal containers, possibly due to the limited efficacy of using radio-frequency electromagnetic sterilization to sterilize the plastics. It would be desirable to provide more efficient and efficacious methods of separating, sterilizing and reclaiming plastics from plastic comingled with infectious waste. Aside from limitations inherent in the radio-frequency electromagnetic radiation to sterilize plastics comingled and contaminated with infectious waste, there is a lack of coordinated efforts to reclaim and recycle plastics comingled with infectious waste. Thus, while recycling techniques such as the type described in U.S. Pat. No. 5,833,922 exist, it is not believed that such techniques have been used to manufacture medical devices. Accordingly, it would be advantageous to provide improved systems and methods for the coordination of such reclamation and recycling efforts. Therefore, there is a need to develop methods of recycling infectious medical waste into new medical devices.

SUMMARY

One or more embodiments of the invention are directed to methods of making a recycled medical device. A plastic resin is obtained from a sterile shredded plastic medical waste material recovered from a mixture of plastic medical waste containers containing medical waste in which shredding and sterilizing are performed substantially simultaneously. The plastic resin is formed into the recycled medical device.

In a detailed embodiment, the shredding and sterilizing are performed in a liquid medium. In specific embodiments, the plastic is separated from the metal and/or glass by float-sink a technique. In more specific embodiments, substantially only water and steam are used to sterilize and shred the used medical waste container.

In specific embodiments, the plastic resin comprises substantially only polypropylene and polyethylene. In some detailed embodiments, the methods further comprise formulating (or reformulating) the plastic resin prior to forming the recycled medical device.

In one or more embodiments, greater than about 60% of the polypropylene and polyethylene in the used medical waste container is recovered from the plastic medical waste container.

In some embodiments, the method further comprises obtaining the plastic medical waste container from a medical facility. In detailed embodiments, the method further comprises scheduling routine pickup of the plastic medical waste container from the medical facility.

In specific embodiments, the recycled medical device is selected from the group consisting of a waste container, a non-fluid path medical device and a fluid path medical device. In detailed embodiments, the plastic medical waste container is a sharps container comprising molded plastic, glass components and metal components. In very specific embodiments, the medical waste contained in the plastic medical waste container comprises infectious waste.

Additional embodiments of the invention are directed to medical devices formed from plastic obtained from reclaimed plastic obtained from medical waste that has been shredded and sterilized substantially simultaneously. The plastic being reclaimed from comingled infectious medical waste selected from the group consisting of rubber, mixed plastics, metal, glass and combinations thereof and the medical waste.

In specific embodiments, the plastic has been reclaimed from a composite of plastic and one or more of glass and metal. In detailed embodiments, the used medical waste comprises a sharps container comprising plastic and one or more of glass and metal.

Further embodiments of the invention are directed to methods of recycling used medical material. Supply of medical waste containers to a medical facility is coordinated. Collection of used medical waste containers from the medical facility is coordinated. Reclamation of plastics from the used medical waste containers is coordinated to provide reclaimed plastic. Manufacture of recycled medical devices from the reclaimed plastic is coordinated. Supply of the recycled medical devices to the medical facility is coordinated. In specific embodiments, the used medical waste containers contain infectious waste.

In detailed embodiments, the medical devices are provided at a lower price than medical devices manufactured from virgin plastics, and each of the coordinating steps are performed by a single entity.

In specific embodiments, recycling of plastics from the used medical waste containers comprises a technique which substantially simultaneously shreds and sterilizes the waste. In more specific embodiments, recycling of plastics from the used medical waste container comprises separating plastics from the shredded waste using a float-sink technique.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

As used in this specification and the appended claims, the term "medical device" refers to any medical device including but not limited to medical waste containers, non-fluid path devices and fluid path devices. Suitable medical devices include, but are not limited to, medical waste containers (e.g., sharps containers, pharmaceutical waste, RCRA containers and chemotherapy containers), hypodermic syringes, catheters, flush syringes, urine cups, plastic tubes, pour bottles and sterilization wraps. Fluid path medical devices include hypodermic syringes, catheters, flush syringes, plastic tubes, and fluid collection tubes, and specifically exclude sharps waste containers.

As used in this specification and the appended claims, the term "medical waste" refers to comingled medical waste including one or more of plastic, molded plastic components, rubber, glass, metal and blood. Examples of medical waste include, but are not limited to, used sharps containers which contain plastic and one or more of glass, metal, rubber and blood.

As used in this specification and the appended claims, the term "coordinating" means planning and directing specified activities, either by conducting the activities directly, or by directing specific activities to be conducted by others. Coordinating may include, but is not limited to conducting, causing to happen, placing an order for, purchasing, receiving an order for, selling and the like. For example, coordinating collection of medical waste containers can include, but is not limited to, picking up the medical waste containers personally, sending an employee to pick up the waste containers and asking an employee of a separate company to pick up the waste containers. In one or more embodiments, the coordinating may be conducted by a single entity, for example, a medical device manufacturer and/or supplier. Thus, the medical device supplier/manufacturer is a central entity in a recycling scheme as described further below.

As used in this specification and the appended claims, "reclamation", "reclaim" and "reclaiming" refer to the recovery of useful substances from waste products. A specific example of a reclamation process involves the recovery of usable plastic material from a mixture of plastic waste mixed with contaminated infectious medical waste. As used in this specification and the appended claims, "recycle" or "recycling" means the act of processing used or waste materials for use in creating new products. As will be understood from a reading of the specification, a recycling operation that recycles used plastic devices will involve reclamation of plastic material from the used plastic devices and creating new products from the reclaimed plastics, that is recycled products.

One or more embodiments of the invention are directed to methods of making recycled medical devices. The methods comprise obtaining plastic resin from a sterile shredded plastic medical waste material reclaimed from a mixture of plastic medical waste containers containing medical waste. The plastic resin is formed into recycled medical devices. In specific embodiments, the medical waste contained in the plastic medical waste container includes infectious waste.

In detailed embodiments, the sterile shredded plastic medical waste material is shredded and sterilized substantially simultaneously, preferably in a liquid medium thereby enhancing the efficiency and efficacy of the operation. Suitable techniques for shredded and sterilizing include, but are not limited to, techniques employed by Red Bag Solutions, Baltimore, Md. (www.redbag.com). Briefly, the Red Bag Solutions process seals infectious waste in a tank. Steam and superheated water are added to the tank. The waste is soaked and a pump grinder draws the waste through a cutter and the pump impeller to shred the material. The shredded material is returned to the tank and continually cut into smaller pieces while circulating through the system. Once the waste is thoroughly shredded, the waste stream is heated to, and held at, about 272° F. for about six minutes. Cold water is then injected into the system to cool the waste which is discharged into a filter to separate the solid from liquid waste. For more information on the Red Bag Solutions process, see www.redbag.com/site/Corp/how.htm. In a specific embodiment, the medical waste containers containing the medical waste are sterilized using substantially only liquid water and steam. A particular benefit of this process prevents the addition of undesirable chemicals to the waste. In addition, a system that uses liquid water and steam is that that the process is odorless, results in minimal to no degradation of the plastic material, and enables shredding and sterilization to be performed substantially simultaneously. The substantially simultaneously shredded and sterilized material is free of offensive odors or visible signs of blood.

The shredded and sterilized waste is combination of the plastic waste container and the contents of the container. The plastic must be reclaimed from this mixture before it can be recycled. In a specific embodiment, the plastic is reclaimed from the metal and/or glass, or other components, by float-sink techniques. In float-sink separation, the waste is placed into a bath having known specific gravity. The waste material with a lower specific gravity than the bath will float, while material with a greater specific gravity will sink. For example, the shredded sterilized waste may be placed into a bath having a specific gravity greater than that of polypropylene. This will result in the polypropylene, and polyethylene which has an even lower specific gravity, to float to the surface of the bath. The glass, metal and other plastics may sink to the bottom. The specific gravity of the bath can be altered with various additives to selectively separate various plastic species from the shredded sterilized waste. One particular advantage to simultaneous shredding and sterilization is that the waste would otherwise need to be shredded before sterilization, resulting in contamination of the shredding equipment. Additionally, the simultaneous shredding and sterilization process does not require separate washing processes or an elutriator.

In detailed embodiments, the plastic resin comprises substantially only polypropylene and polyethylene. The composition of the plastic separated from the previously described processes will be dependent on the medical waste being sterilized. Each batch of medical waste that is sterilized and separated can have a different polypropylene/polyethylene ratio. This ratio may need to be adjusted, depending on the specifications of the product to be manufactured. In specific embodiments, the plastic resin obtained from the recycled medical waste may be reformulated to adjust the ratio of plastic components, to remove some components, or to add additional components.

In detailed embodiments, greater than about 60% of the polypropylene and polyethylene in the used medical waste container is reclaimed and incorporated into the recycled medical device. In detailed embodiments, greater than about 60% of the polypropylene and polyethylene in the used medical waste container is recovered from the recycling process. In other detailed embodiments, greater than about 50%, 70%, 80% or 90% of the polypropylene and polyethylene in the used medical waste container is recovered.

Detailed embodiments further comprise collecting the medical waste container from a medical facility. This can be done, for example, through scheduled routine pickups or by shipping the waste container to the recycler. In specific embodiments, the medical waste is picked up from the medical facility. More specific embodiments further comprise scheduling routine pickup of the medical waste container from the medical facility.

Additional embodiments of the invention are directed to medical devices formed from plastic obtained from shredded recycled sterilized medical waste separated from comingled infectious medical waste selected from the group consisting of rubber, mixed plastics, metal, glass and combinations thereof. In specific embodiments, the plastic was separated from a composite of plastic and one or more of glass and metal. In detailed embodiments, the used medical waste is a sharps container comprising plastic and one or more of glass and metal.

Further embodiments of the invention are directed to methods of recycling used medical material. These methods also protect the environment and keep waste material from the landfills. The methods comprise coordinating supply of medical waste containers to a medical facility; coordinating collection of used medical waste containers from the medical facility; coordinating recycling of plastics from the used medical waste containers; coordinating manufacture of recycled medical devices from the recycled plastic; and coordinating supply of the recycled medical devices to the medical facility.

In one aspect of the invention, a single entity coordinates, that is orchestrates or directs the reclamation and recycling effort. In a specific embodiment, the single entity is a medical device manufacturer or medical device supplier. The medical device manufacturer or supplier coordinates the various activities that comprise the reclamation and recycling scheme, as described further below.

In a specific embodiment, an entity coordinates the supply of medical waste containers to a medical facility such as a hospital, clinic, university, doctor's office or other facility that utilizes medical waste containers. After the medical waste containers are used or filled with medical waste including infectious waste, they can be disposed of in a manner that facilitates their collection for recycling efforts. One step in the recycling scheme involves coordinating collection of used medical waste containers from the medical facility, which can be achieved in a variety of ways. This includes, but is not limited to, an entity itself picking up the containers, for example, having an employee pick up the containers, or by directing or requesting a third party to pick up the medical waste containers, including paying the third party to do so.

Another step in the scheme involves coordinating the reclamation of plastics from the used medical waste containers to provide reclaimed plastic. This can be achieved by having the entity that collects the used waste containers deliver them to a facility that handles reclamation and/or recycling of mixed waste such as mixed medical waste. It will be appreciated that it may be desirable and cost efficient for the coordinating entity or coordinator to set up a reclamation or recycling operation very close to or adjacent the medical facility to shorten delivery time and costs. In some instances in which the reclamation process for reclaiming and sterilizing the plastic is relatively clean and odor free, it may be possible to perform the reclamation operation within the medical facility, for example, in a separate wing of the medical facility or in the basement. Alternatively, the reclamation effort can be coordinated to occur close to, adjacent or within the manufacturing plant where the reclaimed plastic will be utilized to manufacture recycled medical devices. Of course, neither or these scenarios are necessary to the operation, but may be desired to enhance the efficiency and cost of the overall scheme. The reclaimed material can be in any suitable form such as shredded plastic, plastic chips, plastic pellets, plastic flakes, etc.

The reclaimed plastic material is used to make recycled medical devices. The medical device manufacturer or supplier can coordinate the manufacture of recycled medical devices in a variety of ways. For example, the manufacturer may have the reclaimed plastic shipped to one of its facilities to be used in a medical device manufacturing process. The reclaimed plastic may be used to make a device that is comprised in its entirety of the reclaimed plastic, or a portion of reclaimed plastic, depending on the specification of the medical device. In another embodiment, coordinating may involve directing the reclaimed plastic to a third party for use in the manufacture of a recycled medical device. Again, the recycled medical device made can be made entirely of the reclaimed plastic, or a fraction of the material that makes up the recycled device may be reclaimed plastic.

The manufactured recycled medical devices are then supplied to a medical facility. Preferably, this is a coordinated supply activity, which may be performed by the single entity, for example, the medical device manufacturer or supplier. Thus, coordinating supply of the recycled medical devices to the medical facility includes, but is not limited to, selling or giving the devices to the medical facility personally, or asking/paying a different person or company to do so.

Thus, the above described scheme provides for a coordinated and comprehensive way of ensuring that plastic within medical waste is reclaimed, recycled into new products and supplied to medical facilities. The scheme according to one embodiment is facilitated by coordination by a single entity.

In detailed embodiments, the medical devices are provided at a lower price than medical devices manufactured from virgin plastics. In specific embodiments, the used medical waste containers contain infectious waste.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of making a recycled medical device comprising forming a recycled medical device from a recycled plastic resin produced by shredding and sterilizing in a single pressurized tank a mixture of plastic medical waste containers containing medical waste soaked in superheated water and steam and circulated through a cutter.

2. The method of claim 1, wherein the plastic resin is separated from the metal and/or glass by float-sink a technique.

3. The method of claim 1, wherein the plastic resin comprises only polypropylene and polyethylene.

4. The method of claim 1, further comprising formulating the plastic resin prior to forming the recycled medical device.

5. The method of claim 1, wherein the used plastic medical waste containers comprise polypropylene and polyethylene, and greater than about 60% of the polypropylene and polyethylene is recovered and incorporated into the recycled medical device.

6. The method of claim 1, wherein the plastic medical waste containers are obtained from a medical facility.

7. The method of claim 1, wherein the recycled medical device is selected from the group consisting of a waste container, a non-fluid path medical device and a fluid path medical device.

8. The method of claim 1, wherein the contents of the plastic medical waste containers comprises molded plastic, glass components and metal components.

9. The method of claim 1, wherein the medical waste contained in the plastic medical waste containers comprises infectious waste.

10. The method of claim 1, wherein the shredded waste is heated to a temperature of about 272° F.

11. The method of claim 10, wherein the shredded waste is held at about 272° F for about 6 minutes.

12. The method of claim 1, wherein the shredded waste does not require a separate washing process.

* * * * *